United States Patent [19]

Hyttinen

[11] Patent Number: 5,016,264
[45] Date of Patent: May 14, 1991

[54] TRANSFER METHOD AND ARRANGEMENT FOR A FILM CASSETTE UNIT IN A PANORAMIC X-RAY APPARATUS

[75] Inventor: Klaus Hyttinen, Kerava, Finland
[73] Assignee: Instrumentarium Corp., Finland
[21] Appl. No.: 447,016
[22] Filed: Dec. 6, 1989

[30] Foreign Application Priority Data

Mar. 21, 1989 [FI] Finland .................................. 891320

[51] Int. Cl.$^5$ .............................................. A61B 6/14
[52] U.S. Cl. .......................................... 378/38; 378/39; 378/197; 378/177
[58] Field of Search ................ 378/38, 177, 179, 181, 378/182, 39, 40, 187, 198, 208

[56] References Cited

U.S. PATENT DOCUMENTS

| | | | |
|---|---|---|---|
| 2,798,958 | 7/1957 | Hudson et al. | 378/39 |
| 3,045,118 | 7/1962 | Hollman et al. | 378/39 |
| 4,449,225 | 5/1984 | Tammisalo | 378/39 |
| 4,675,888 | 6/1987 | Gästrin | 378/38 |
| 4,741,007 | 4/1988 | Virta et al. | 378/39 |
| 4,813,060 | 3/1989 | Heubeck et al. | 378/39 |
| 4,852,134 | 7/1989 | Kinanen et al. | 378/38 |
| 4,907,251 | 3/1990 | Mork et al. | 378/38 |

FOREIGN PATENT DOCUMENTS

| | | |
|---|---|---|
| 1955294 | 5/1970 | Fed. Rep. of Germany . |
| 69711 | 9/1980 | Finland . |
| 73361 | 8/1985 | Finland . |

*Primary Examiner*—Edward P. Westin
*Assistant Examiner*—Kim-Kwok Chu
*Attorney, Agent, or Firm*—Andrus, Sceales, Starke & Sawall

[57] ABSTRACT

The invention relates to a transfer method and an arrangement for a film cassette unit in a panoramic X-ray apparatus. A film cassette unit (6), comprising a film cassette and cassette aggregate, is transferred either manually or electrically upwards from between patient and operator. After positioning a patient, prior to effecting the imaging, the film cassette unit (6) is lowered or descends automatically down to an imaging position. The transfer can be effected either by turning around a horizontal shaft (9) or by moving in vertical plane.

7 Claims, 1 Drawing Sheet

TRANSFER METHOD AND ARRANGEMENT FOR A FILM CASSETTE UNIT IN A PANORAMIC X-RAY APPARATUS

BACKGROUND OF THE INVENTION

In panoramic imaging, a film cassette unit which includes a film cassette and a cassette stand and/or a cassette aggregate is fixedly positioned either entirely or partially between the operator and an object to be imaged. There is no possibility of transferring the film cassette unit in vertical direction, i.e. up and down. Thus, the operator does not have a clear visibility directly from the side to the head and cervical column of a patient. In addition, the operator must reach from below or behind a cassette aggregate for straightening the head and cervical column of a patient. The patient is forced to step first into and then, after the imaging, out of the imaging apparatus between X-ray tube and cassette unit and in several cases even slightly around the cassette unit.

In the prior art equipment the above problems have been resolved only partially or not at all. In the imaging apparatus disclosed in published EP application 229 308, a film cassette unit can be pivoted around a vertical axis which to some extent improves the visual contact between operator and patient. However, the film cassette unit which has been turned aside still partially blocks visibility and also impedes working as well as restricts the stepping of a patient in and out of the imaging apparatus. In other prior known equipment the film cassette unit is fixedly positioned at and above the shoulder (right or left) of a patient, blocking the lateral visibility and impeding the ergonomical working conditions of the operator.

A benefit in this prior known arrangement is that the cassette aggregate is in a way ready for imaging (except for equipment in which a film cassette must be moved inside the cassette aggregate to a start position).

SUMMARY OF THE INVENTION

An object of the invention is to provide a transfer methos for a film cassette unit in a panoramic X-ray apparatus and a transferable arrangement which make it possible that there will be no barriers to visibility or working between patient and operator as a patient steps into the imaging apparatus, during the positioning of a patient, and as a patient steps out after the imaging.

DESCRIPTION OF THE DRAWINGS

The invention will now be described with reference made to the accompanying drawings, in which.

DESCRIPTION OF THE ILLUSTRATED EMBODIMENT

Figure 1:
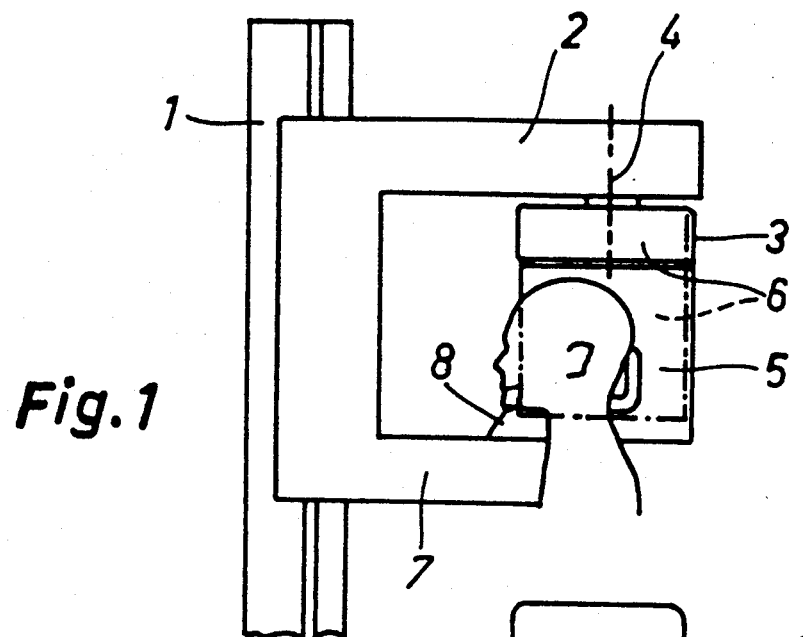
FIG. 1 is a side view of a panoramic X-ray apparatus provided with a transferable arrangement of the invention for a film cassette unit.

The panoramic X-ray apparatus includes a main column 1 which carries horizontal consoles 2 and 7, the height of the latter being vertically adjustable. Suspended from the upper horizontal console 2 upon a pivoted shaft 4 is a bracket arm 3, one of its ends carrying an X-ray tube 5 and the other a film cassette unit 6. The lower horizontal console 7 carries head supporting means 8 for securing the head firmly in an imaging position between X-ray tube 5 and film cassette unit 6. During the imaging, arm 3 rotates around shaft 4, whereby the film cassette unit 6, which has been set in an imaging position shown by dash-and-dot lines, travels around the chin arch of a patient and the X-ray tube 5 travels accordingly around the neck of a patient. In addition to the rotating motion around shaft 4, bracket arm 3 may perform a linear motion or some other type of motion combined with rotating movement for focusing the X-rays as orthogonally as possible towards the chin arch.

The film cassette unit 6 includes a film cassette and a cassette stand for placing the film cassette thereupon. The cassette unit 6 further includes a cassette aggregate for transferring the film cassette as well as its film at a certain speed in a horizontal direction during the imaging. The film transfer speed is in a certain proportion to the rotating speed of bracket arm 3 in order to image on film a desired layer of the chin arch.

According to the invention, the film cassette unit 6 is so connected with a rotating bracket 3 that said film cassette unit 6 can be swung or moved to an upper position for not building a visibility or working impediment between patient and operator during the positioning of a patient and a patient need not walk around the film cassette unit for stepping in or out of the imaging apparatus.

Figure 2:
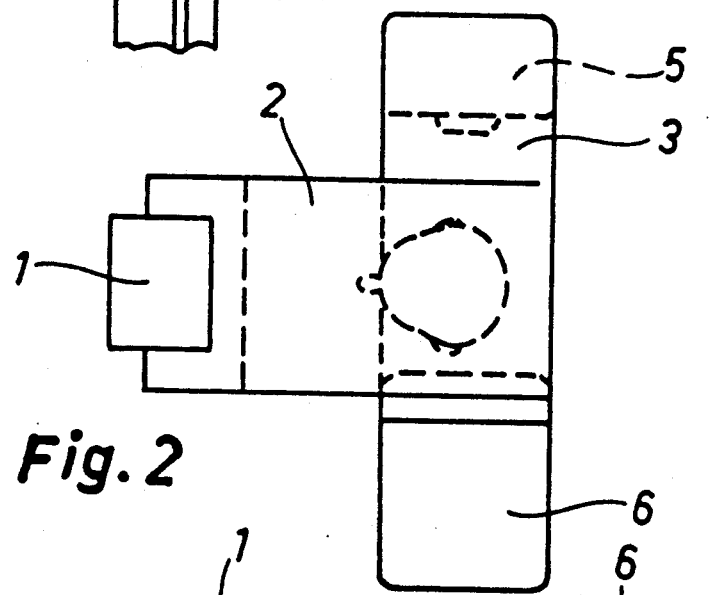
FIG. 2 shows the apparatus of FIG. 1 in a plan view.
Figure 3:
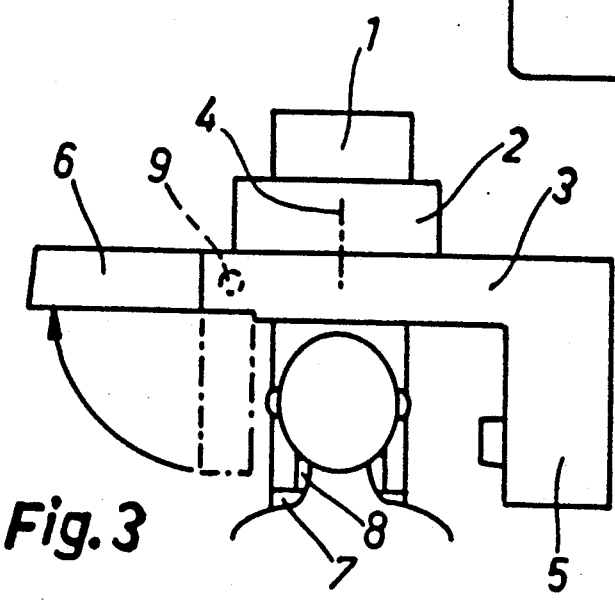
FIG. 3 shows the same apparatus in a rear/front view.

In the case shown in FIGS. 1-3, a film cassette unit 6 is adapted to be rotated between a horizontal upper position and a vertical lower position around a pivoted shaft 9. The rotating motion can be effected manually or with electric power. If the rotating motion is to be effected manually, this requires locking means between rotating arm 3 and cassette unit 6 for retaining film cassette unit 6 in upper position and in lower position with a certain clamping force. When turned to the upper position, said film cassette unit 6 can be adapted to be partially inserted or driven inside said rotating arm 3.

Figure 4:
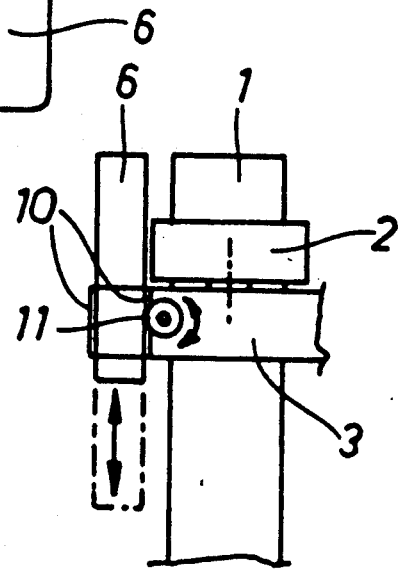
FIG. 4 shows an alternative way of transferring a film cassette unit in a view similar to FIG. 3.

In the case of FIG. 4, a film cassette unit is adapted to be transferred in a vertical plane along vertical guides 10, the transfer movement being effected by means of a drive motor 11.

The basic position of a film cassette unit 6 is at the top. After setting a patient properly in position and upon pressing the imaging release button, the film cassette unit descends to the level of a patient's shoulder and the X-rays are switched on. At the end of an imaging session, the film cassette unit ascends from between patient and operator for giving the patient an unblocked exit from the imaging apparatus. The film cassette with its exposed film is removed from the cassette aggregate and the film is developed. The rotating bracket arm 3 is returned to a start position which is why the film cassette unit 6 must be temporarily transferred to the lower position. A fresh loaded film cassette is inserted into cassette unit 6 and another patient can be positioned for treatment.

If desired, the cassette unit 6 can be kept locked in a ready-to-shoot position (lower position).

The invention eliminates completely the problems involving lateral visibility and ergonomics of the operator, since the film cassette and cassette aggregate ate not positioned between patient and operator but in an upper position above the head of an operator. A further advantage is that the film cassette unit 6 rises to an upper position when proceeding from panoramic imaging technique to lateral and pa-imaging techniques of the skull.

In addition to dental imaging, the invention can also be applied to various methods of imaging maxillary joints and sinus cavities which are also based on panoramic technique and a certain type of positioning of a patient for imaging.

The number of lateral skull imagings and pa-imagings (pa=projecting direction postero-anterios) is less and the most popular application is the panoramic technique based imaging of teeth, maxillary joints and sinus cavities, representing 90% of all imagings effected with the apparatus.

I claim:

1. In an panoramic X-ray apparatus, a support column, frame means mounted for vertical movement on said support column, elongated bracket means mounted for rotation on said frame means about a vertical axis, an X-ray tube disposed on one end of said bracket means and having a horizontal aperture axis, a film cassette unit connected to the opposite end of said bracket means, support means disposed on said bracket means between said X-ray tube and said film cassette for supporting the head of a patient between said X-ray tube and said film cassette unit, and mounting means for mounting said film cassette unit for movement relative to said bracket means from an operative position where said film cassette unit is in alignment with said axis to an inoperative position where said film cassette unit is located above and out of alignment with said axis.

2. The apparatus of claim 1, wherein said frame means includes an upper leg and a generally parallel lower leg, said bracket means being mounted for rotation on said upper leg and said support means being mounted on said lower leg.

3. The apparatus of claim 1, wherein said mounting means comprises means for pivoting said film cassette unit about a horizontal axis on said bracket means for movement between said operative and inoperative positions.

4. The apparatus of claim 1, wherein said mounting means comprises means for moving said film cassette unit in a vertical linear path between said operative and inoperative positions.

5. The apparatus of claim 4, and including guide means on said bracket means for guiding said film cassette unit in movement in said linear path.

6. The apparatus of claim 1, and including locking means for locking said film cassette unit in said operative and inoperative positions.

7. The apparatus of claim 3, wherein said film cassette unit when in said operative position is disposed vertically and extends downwardly from said bracket means and said film cassette unit when in said inoperative position extends horizontally and is aligned with said bracket means.

* * * * *